United States Patent
Yokubinas et al.

(10) Patent No.: US 11,000,462 B2
(45) Date of Patent: May 11, 2021

(54) LIQUID CLEANSING COMPOSITION

(71) Applicant: Conopco, Inc., Englewood Cliffs, NJ (US)

(72) Inventors: Leonora Yokubinas, Avon, CT (US); Jessica Ann Krisiak, Stamford, CT (US); Kevin David Hermanson, Woodbridge, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/615,434

(22) PCT Filed: May 25, 2018

(86) PCT No.: PCT/EP2018/063792
§ 371 (c)(1),
(2) Date: Nov. 21, 2019

(87) PCT Pub. No.: WO2018/219812
PCT Pub. Date: Dec. 6, 2018

(65) Prior Publication Data
US 2020/0170909 A1   Jun. 4, 2020

(30) Foreign Application Priority Data
Jun. 2, 2017   (EP) ..................................... 17174361

(51) Int. Cl.
| | |
|---|---|
| *A61K 8/36* | (2006.01) |
| *A61K 8/19* | (2006.01) |
| *A61K 8/34* | (2006.01) |
| *A61K 8/365* | (2006.01) |
| *A61K 8/60* | (2006.01) |
| *A61Q 19/10* | (2006.01) |

(52) U.S. Cl.
CPC ................ *A61K 8/361* (2013.01); *A61K 8/19* (2013.01); *A61K 8/345* (2013.01); *A61K 8/365* (2013.01); *A61K 8/602* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 2,950,248 A * | 8/1960 | Armstrong | C10M 5/00 508/522 |
| 5,876,705 A | 3/1999 | Uchiyama et al. | |
| 5,885,948 A | 3/1999 | Glenn, Jr. et al. | |
| 6,080,707 A | 6/2000 | Glenn, Jr. et al. | |
| 6,080,708 A | 6/2000 | Glenn, Jr. et al. | |
| 6,730,643 B2 | 5/2004 | Chokappa et al. | |
| 2001/0018068 A1* | 8/2001 | Lorenzi | A61K 8/0208 424/443 |
| 2010/0074879 A1* | 3/2010 | Aoki | A61P 17/18 424/94.1 |

FOREIGN PATENT DOCUMENTS

JP         59227999         12/1984

OTHER PUBLICATIONS

Search Report and Written Opinion in EP17174361; dated Jul. 26, 2017.
Search Report and Wrtitten Opinion in PCTEP2018063792; dated Jul. 3, 2018; World Intellectual Property Org. (WIPO).
Written Opinion 2 in PCTEP2018063792; dated Apr. 26, 2019; World Intellectual Property Org. (WIPO).
IPRP2 for PCTEP2018063792; dated Aug. 5, 2019.

* cited by examiner

*Primary Examiner* — Sin J Lee
(74) *Attorney, Agent, or Firm* — Edward A. Squillante, Jr.

(57) ABSTRACT

The present invention relate to liquid cleansing compositions comprising 12-HSA which are both processable and stable. Applicants have defined a specific composition window (defined by specific types and ratios of fatty acid and/or fatty acid soaps, as well as critical ceiling for 12-HSA and floor levels of polyol) where these objectives can be met.

13 Claims, No Drawings ical compositions comprising 0.5 to 10% by wt. of crystalline hydroxyl-containing liquids including 12-HSA as liquid stabilizer. None disclose fatty acid based compositions; none recognize problems associated with such compositions; and none contemplate the specific solutions of our invention (i.e., window of myristic acid, floor levels of polyol).

LIQUID CLEANSING COMPOSITION

FIELD OF THE INVENTION

The present invention relates to liquid cleansing compositions and particularly to compositions which are processable, stable and which deliver consumer benefits (e.g., moisturization, skin lightening) to the skin.

BACKGROUND OF THE INVENTION

In liquid cleansing compositions suitable for the consumer, the compositions should be processable (e.g., have a rheology such that all ingredients can be mixed without the mixing blade getting stuck), stable (e.g., not phase separate over a defined time at a defined temperature), and have rheological properties that provide a suitable sensory experience. It is desirable to add ingredients having skin health or other benefits.

One molecule that is particularly beneficial for incorporation into such liquids is 12-hydroxystearic acid ("12-HSA"). 12-HSA is a well-known peroxisome proliferator-activated receptor ("Ppar") activator than can influence skin health.

However, incorporation of 12-HSA into liquid formulations provides challenges because it can impact formulation structuring, formulation viscosity, processing and stability. In the absence of any direction on how to incorporate, use of 12-HSA typically will lead to thickening or thinning of the formulation and/or to phase separation (instability) over time.

Specifically, in formulations with low synthetic surfactant concentration, predominantly fatty acid and fatty acid soap based compositions (i.e., compositions having the combination of fatty acid and fatty acid soap, preferably $C_8$ to $C_{20}$ fatty acids and soaps, which is greater than 50% of the combination plus other surfactant), the use of 12-HSA typically will lead to compositions which are not processable, not stable (i.e., not "stress" stable as defined), or both.

Quite surprisingly and unexpectedly, applicants have found a formulation window wherein, in such predominantly fatty acid and fatty acid soap based, low synthetic surfactant compositions, 12-HSA can be used while compositions retain both processability and stability. The formulation window comprises specific selection of fatty acids such that specific amounts of myristic acid (from 45 to 65% by wt. of all fatty acids used) must be used in combination with a floor level (20% or greater, preferably 21 to 40%, most preferably 25 to 35% by wt. of compositions) of polyol. Compositions which do not fall within this specific myristic acid window or which do not have floor levels of polyol (e.g., glycerine, polyalkylene glycols) do not meet requirements of both processability and stability.

The use of 12-HSA in soap bar compositions is not new.

U.S. Pat. No. 6,730,643 to Chokappa et al. discloses transparent soap bars comprising 30 to 60% total fatty matter ("TFM") wherein from 1 to 15% by weight is the salt of 12-hydroxystearic acid or a precursor thereof. These compositions are bars and issues of stability, for example, and selection of myristic acid at defined level of fatty acid to stabilize liquid compositions are irrelevant.

U.S. Pat. No. 5,876,705 to Uchiyama et al. discloses conditioning shampoos, which may comprise 0.9 to 10% fatty compounds, including 12-HSA. These are not fatty acid based systems and neither problems associated with compositions of the invention, nor the solutions, are contemplated.

U.S. Pat. Nos. 5,885,948; 6,080,707; and 6,080,708, each to Glenn, Jr. et al., each discloses liquid compositions comprising 0.5 to 10% by wt. of crystalline hydroxyl-containing liquids including 12-HSA as liquid stabilizer. None disclose fatty acid based compositions; none recognize problems associated with such compositions; and none contemplate the specific solutions of our invention (i.e., window of myristic acid, floor levels of polyol).

SUMMARY OF THE INVENTION

The present Invention provides liquid cleansing compositions comprising:
1) 10 to 45% by wt. $C_8$ to $C_{20}$, preferably $C_{10}$ to $C_{20}$ or $C_{12}$ to $C_{18}$ fatty acid or fatty acid soap (which includes 0.1 to 5% 12-HSA of point (3) below) wherein 45 to 65%, preferably 50 to 63%, more preferably 55 to 62% of the total fatty acid is $C_{14}$ myristic acid;
2) less than 5% by wt. synthetic surfactant, preferably 1 to 3% by wt.;
3) 0.1 to 5% by wt., preferably 0.5 to 4% by wt. 12-hydroxystearic acid (12-HSA), wherein the 0.1 to 5% 12-HSA is part of the 10 to 45% fatty acid of paragraph (1) above;
4) 20 to 50% by wt., preferably 21 to 40%, more preferably 25 to 35% by wt. polyol; and
5) 0 to 5%, preferably 0.01 to 3%, preferably 0.03 to 2% by wt. cationic polymer;

wherein the pH of said liquid cleanser composition is 8.0 to 11.0, preferably 8.5 to 10.0.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

The present invention relates to liquid cleansing compositions, particularly predominantly fatty acid soap plus fatty acid based liquids comprising 12-HSA as benefit agent. 12-HSA is a well-known Ppar activator that can influence skin health.

However, 12-HSA can impact formulation structuring, rheology, processing and/or stability (e.g., forming product which phase separates).

Applicants have found that, if fatty acids and fatty acid soaps in the final composition are selected to fall within defined composition and ranges (in a fatty acid plus fatty acid soap based, low synthetic surfactant composition), and polyol is kept at defined floor levels (use of at least certain amount required), 12-HSA can be incorporated such that it is processable and the final composition is stable, wherein "processable" and "stability" are defined below.

Fatty Acid

Compositions of the invention comprise 10% to 45%, preferably 20 to 45%, more preferably 25 to 45% by wt. of fatty acid or fatty acid soap. The chain length of the fatty acid or fatty acid soap is $C_8$ to $C_{20}$, preferably $C_{10}$ to $C_{20}$ or $C_{12}$ to $C_{18}$. The 10 to 45% amount includes 0.1 to 5% of 12-HSA.

Applicants have found a unique window of myristic acid required to incorporate 12-HSA and maintain processability, stability or both. Specifically, 45% to 65%, preferably 50 to 63%, more preferably 55 to 62% of the free fatty acid (unneutralized fatty acid) must be $C_{14}$ (myristic) fatty acid.

Surfactant

The particular type of co-surfactant that may be used as co-surfactant in the predominantly fatty acid and fatty acid soap based compositions of the invention is not critical. It may be any anionic, non-ionic, amphoteric and/or zwitterionic surfactant as are well known to those skilled in the art. It is important only that these are low synthetic surfactant systems which comprise, for example, 0 to 5%, preferably 0.5 to 4%, more preferably 1 to 3% by wt. of the composition.

12-HSA

Compositions of the invention comprise 0.1 to 5%, preferably 0.5 to 4% by wt. 12-hydroxystearic acid. This is part of the 10% to 45% fatty acid plus fatty acid soap. As indicated, typically, use of 12-HSA in low synthetic surfactant, fatty acid plus fatty acid soap based compositions results in processing issues and phase instability. Preferably, selection of types and amounts of fatty acid plus fatty acid soap and polyol permit 12-HSA to be processed and maintained as a stable formulation.

Polyol

Another important component of formulations for the invention is that they comprise greater than 20%, preferably 21 to 40%, more preferably 25 to 35% by wt. polyol. Insufficient polyol, even when types and amount of fatty acid are properly selected, leads to stress instability, and consequent phase separation.

Preferred polyols include glycerine and short chain alkylene glycols such as, for example, propylene or ethylene glycol.

Other Components

In addition to 12-HSA, compositions of the invention may contain, for example, 0 to 15%, preferably 0.1 to 10% or 0.1 to 5% by wt. of a skin benefit agent which may include oil soluble emollients or moisturizing oils. These molecules may increase hydration by preventing water loss (occlusive), attracting moisture (humectant) or by restoring moisturizing factors to skin (e.g., amino lipids).

Examples of moisturizers include petrolatum, silicone and vegetable or triglyceride oils. Restorative agents include vitamins (vitamins A or E); lipids (e.g., cholesterol), vegetable butters (shea butter), and minerals, minerals as zinc or magnesium.

Compositions may contain 0.1 to 7% of a structurant. These may include, for example, carbohydrate gums (e.g., cellulose gum), polyacrylates (e.g., Carbopol®, Aculyn® polymer), or mixtures thereof.

Compositions also may contain 0.01 to 2% or 1% of preservative (e.g., parabens, methyl-isothiozolinones, benzoic acid, phenoxy ethanol and mixtures thereof).

Optionally, they may contain one or more additional ingredients. Non-limiting examples of such additional ingredients are, for example, colorants, pigments, opacifiers, fragrance (whether encapsulated or present as free-fragrance), emotive oils, vitamins and vitamin derivatives, abrasives, optical agents (including for example, reflective particles and interference pigments), pH adjusters, plant extracts, essential oils, preservatives, antioxidants, antimicrobials, viscosity modifiers, humectants, beard wetting agents, sensory agents, fatty acid soap, and skin and/or hair benefit agents (e.g., aloe, allantoin, panthenol, alpha-hydroxy acids, phospholipids, botanical oils, and amino acids to name a few). The selection and amount of any individual additional ingredient depends upon factors that include the particular ingredient, the properties desired, and the intended use of the composition in which it is employed. For example, fragrance is typically employed in an amount of 0.1 to 3.0% by weight of the composition, or higher. For many compositions, the total amount of such additional ingredients is 0.01 to 30% by weight, more particularly, 0.1 to 15% by weight, even more particularly, 1 to 10% by weight, based on the total weight of the composition. In one or more embodiments, the total amount of such additional optional ingredients is 0.5 to 5% by weight.

Compositions are aqueous based and comprise typically 5 to 40%, preferably 8 to 20% by wt. water. Water is balance after all ingredients noted above are accounted for.

Compositions of the invention preferably have pH of 8.0 to 11.0, more preferably 8.5 to 10.0.

In another form, the invention provides a method of providing stable and processable (both as defined) liquid compositions comprising 12-HSA, which method comprises forming compositions of claim 1.

Processing

Compositions of the invention are made as follows:

Fatty acids, polyols, structuring agent (e.g., alkylene glycol distearate), and chelating agent (e.g., EDTA) were combined in a main vessel and heated to 75 to 80° C. As fatty acids melted, mix was agitated. When everything was melted and homogeneous, heat was removed and potassium hydroxide, co-surfactants (e.g., decylglucoside), and cationic polymers were added. After cooling, emotives, perfume, and preservatives were added.

Protocols and Definitions

The term "Processable Liquid Cleanser", is defined as a skin cleansing liquid composition with a rheology such that, when produced in a vessel with mixing blade(s), the product does not become so thick that the blade(s) is no longer able to mix the ingredients.

For purposes of the invention, mixing is done with six (6) blades, and the blades are rectangular in shape, measuring 5 centimeter by 4 centimeters. The blades are spun at 130 to 140 revolutions per minute (rpm).

Under these processing conditions, if the mixer cannot be made to mix at speed of 130 to 140 rpm, the product is considered too "thick" and is unprocessible.

The term "Stress Stable Liquid Cleanser" is defined as a skin cleansing liquid composition that when exposed to 45° C. conditions does not phase separate for at least two weeks.

Examples

The following table includes some non-limiting examples of the present invention. Ingredients are recorded in percent active

| Ingredients | Control Batch | Comp. Example A | Comp. Example B | Example 1 | Comp. Example C | Comp. Example D | Comp. Example E |
|---|---|---|---|---|---|---|---|
| Polyol | 30 | 30 | 30 | 30 | 30 | 10 | 15 |
| C12, C16, C18 Fatty Acids | 8.39 | 14.69 | 7.36 | 8.39 | 8.39 | 8.39 | 8.39 |
| Myristic Acid | 25 | 17.5 | 26.25 | 25 | 25 | 25 | 25 |
| 12-Hydroxystearic Acid | 1.58 | 2.77 | 1.39 | 3.15 | 7 | 1.58 | 1.58 |
| Structuring Agent | 4 | 4 | 4 | 4 | 4 | 4 | 4 |
| Chelating Agent | 0.05 | 0.05 | 0.05 | 0.05 | 0.05 | 0.05 | 0.05 |
| Co-Surfactant | 2.5 | 2.5 | 2.5 | 2.5 | 2.5 | 2.5 | 2.5 |
| Potassium Hydroxide | 7.15 | 7.03 | 7.16 | 7.15 | 7.15 | 7.16 | 7.16 |
| Cationic Polymer | 0.05 | 0.05 | 0.05 | 0.05 | 0.05 | 0.05 | 0.05 |
| Preservative/Perfume/Emotive | 0.65 | 0.65 | 0.65 | 0.65 | 0.65 | 0.65 | 0.65 |
| Water | 10.48 | 10.17 | 10.43 | 8.91 | 5.06 | 30.43 | 25.46 |
| Processable | Yes | No | Yes | Yes | Yes | Yes | Yes |
| Stress Stable | Yes | — | No | Yes | No | No | No |

In Comparative Example A, myristic acid (used at levels of 17.5%) comprises just about 44% (43.9%) of total fatty acid plus fatty acid soap used. The amount is calculated by first calculating the amount of fatty acid soap, i.e., produced from potassium hydroxide, and then calculating amount of myristic over total fatty acid and soap. Specifically, this is noted below:

-Molar mass ratio of potassium to potassium hydroxide:

$$\frac{K}{KOH} = \frac{39.1}{39.1 + 16 + 1} = 69.70\%$$

-Calculate the % potassium that reacts for each condition:

EX) composition A 7.03% KOH added to batch, thus:

$$\frac{69.70}{100} * 7.03 = 4.90\%$$

-Calculate myristic acid ratio $$\frac{\text{Myristic Acid}}{\text{Total } FA + \text{Potassium}} * 100$$

$$\frac{17.5}{[(17.5 + 14.69 + 2.77) + 4.90]} * 100 = 43.9\%$$

It is seen that, at 44% myristic, the composition is not processable, as defined; thus, greater than 44% $C_{14}$ (myristic acid) is needed.

In Comparative B, myristic acid (26.25%) is 75% of total of fatty acid (26.25/26.25+7.36+1.39 (total fatty acid)+5.0 (potassium soap), which is equal to 26.25/40%=65.6%). This comparative fails the stress test; thus, when level of $C_{14}$ is above 65%, myristic acid level is too high.

In Example 1, myristic acid represents 60.18% of total fatty acid (25(myristic)/41.54 (total fatty acid plus soap). This "sweet spot" between 45 and 65% represents an area where compositions are both processable and stable (as we define "stress stable" in protocol).

Comparative C defines a composition where the ratio of myristic to total fatty acid plus soap does fall between 45 and 65% 25/45.39 or 55.8%). However, the level of 12-HSA is 7%; this is above the ceiling level of 5% HSA required by the invention. As seen, this composition is not processable.

Both comparatives D and E again have myristic acid levels falling within critical ratios (greater than 45 to 65%) of total fatty acid plus soap (25/39.97 or 62.5%). Further, levels of 12-HSA also are lower than 5% and fall within levels of invention. However, the levels of polyol (10% and 15%, respectively) are below the floor levels required by the invention and, thus, both compositions are not processable.

In the examples, calculations refer to the ingredients as added. It is noted that, in our examples, only fatty acids were added, not fatty acid soaps. However, were soaps added in forming the calculations, the numerator would change to myristic acid plus myristic acid soap (e.g. any myristic acid soap added or formed on addition) and the denominator would change to total fatty acid+total fatty acid soap (not including potassium soap formed from KOH)+potassium (which is potassium soap formed from KOH as noted). Thus, the 55 to 62% in that case would represent percent by weight of myristic acid plus myristic acid soap over total fatty acid, total fatty acid soap (not including potassium soap formed) and potassium soap.

It is seen that the invention defines a critical space required for compositions to be both processable and stable.

The invention claimed is:

1. A liquid cleansing composition comprising:
   a) 10 to 45% by wt. $C_8$ to $C_{20}$ fatty acid and/or fatty acid soap wherein 45% to 65% of the total wt. % fatty acid and fatty acid soap is $C_{14}$ myristic acid;
   b) less than 5% by wt. synthetic surfactant;
   c) 0.1 to 5% by wt. 12-hydroxystearic acid (12-HSA), wherein the 0.1 to 5% 12-HSA is part of the 10 to 45% by wt. component (a);
   d) 20 to 50% by wt. polyol;
   e) 0 to 5% by wt. cationic polymer; and
   f) water
   wherein the liquid cleansing composition has a pH from 8.0 to 11.0,
   and further wherein the weight percent (amount) of myristic acid is calculated according to the following formula:

$$\frac{\text{Myristic Acid}}{\text{Total } FA + FA \text{ soap}} * 100 = \text{amount (wt \%) of myristic acid.}$$

2. The composition according to claim 1 wherein the composition contains co-surfactant and said co-surfactant is an alkylglucoside.

3. The composition according to claim 1, wherein said polyol is selected from the group consisting of glycerine, alkylene glycol and mixtures thereof.

4. The composition according to claim 1 wherein 20 to 45% by wt. fatty acid or fatty acid soap is present and the fatty acid or fatty acid soap is $C_{10}$ to $C_{20}$.

5. The composition according to claim 1 wherein 25 to 45% by wt. fatty acid or fatty acid soap is present and the fatty acid or fatty acid soap is $C_{12}$ to $C_{18}$.

6. The composition according to claim 1 wherein 50 to 63% of the total fatty acid and fatty acid soap is $C_{14}$ myristic acid.

7. The composition according to claim 1 wherein 55 to 62% of the total fatty acid and fatty acid soap is $C_{14}$ myristic acid.

8. The composition according to claim 1 wherein the synthetic surfactant makes up from 1 to 3% wt. of the composition.

9. The composition according to claim 1 wherein the 12-HSA is present at 0.5 to 4% by wt. of the composition.

10. The composition according to claim 1 wherein the polyol is present at 21 to 40% by wt. and the cationic polymer is present at 0.01 to 3% by wt. of the composition.

11. The composition according to claim 1 wherein the polyol is present at 21 to 40% by wt. and the cationic polymer is present at 0.03 to 2% by wt. of the composition.

12. The composition according to claim 1 wherein the composition further comprises fragrance, oils, plant extracts, antimicrobials, antioxidants or a mixture thereof.

13. A method for producing the liquid cleansing composition according to claim 1, comprising the steps of:
 a) combining fatty acid including $C_{14}$ myristic acid, polyol, water and optional structuring agent and optional chelating agent in a vessel to make a mixture, the fatty acid including 0.1 to 5% 12-HSA based on total weight of the composition;
 b) heating until all ingredients of the mixture of step a) are melted;
 c) adding KOH, optional cationic polymer and optional co-surfactant;
 d) allowing the mixture to cool; and
 d) recovering the liquid cleansing composition,
wherein the composition comprises less than 5% by wt. synthetic surfactant.

* * * * *